(12) United States Patent
Brinker et al.

(10) Patent No.: US 9,233,993 B2
(45) Date of Patent: Jan. 12, 2016

(54) N-PHOSPHONOMETHYLGLYCINE GUANIDINE DERIVATIVE SALTS

(75) Inventors: Ronald J. Brinker, Ellisville, MO (US); Olivier Soula, Venissieux (FR); Alain Lemercier, Venissieux (FR)

(73) Assignees: Monsanto Technology LLC, St. Louis, MO (US); Flamel Technologies (FR)

( * ) Notice: Subject to any disclaimer, the term of this patent is extended or adjusted under 35 U.S.C. 154(b) by 632 days.

(21) Appl. No.: 13/381,457

(22) PCT Filed: Jun. 24, 2010

(86) PCT No.: PCT/US2010/039745
§ 371 (c)(1),
(2), (4) Date: Mar. 23, 2012

(87) PCT Pub. No.: WO2011/008453
PCT Pub. Date: Jan. 20, 2011

(65) Prior Publication Data
US 2012/0172220 A1    Jul. 5, 2012

Related U.S. Application Data

(60) Provisional application No. 61/221,819, filed on Jun. 30, 2009.

(51) Int. Cl.
*C07F 9/22*    (2006.01)
*C07F 9/28*    (2006.01)
*C07F 9/38*    (2006.01)
*A01N 57/20*   (2006.01)
*C07C 279/04*  (2006.01)
*C07C 279/12*  (2006.01)
*C07C 279/02*  (2006.01)

(52) U.S. Cl.
CPC ............. *C07F 9/3813* (2013.01); *A01N 57/20* (2013.01); *C07C 279/02* (2013.01); *C07C 279/04* (2013.01); *C07C 279/12* (2013.01)

(58) Field of Classification Search
CPC .................................................. C07F 9/3813
See application file for complete search history.

(56) References Cited

U.S. PATENT DOCUMENTS

| | | | |
|---|---|---|---|
| 3,799,758 A | 3/1974 | Franz | |
| 3,853,530 A | 12/1974 | Franz | |
| 4,140,513 A | 2/1979 | Prill | |
| 4,315,765 A | 2/1982 | Large | |
| 4,397,676 A * | 8/1983 | Bakel | 504/206 |
| 4,405,531 A | 9/1983 | Franz | |
| 4,475,942 A | 10/1984 | Bakel | |
| 4,481,026 A | 11/1984 | Prisbylla | |
| 4,507,250 A | 3/1985 | Bakel | |
| 5,668,085 A | 9/1997 | Forbes et al. | |
| 5,750,468 A | 5/1998 | Wright et al. | |
| 7,049,270 B2 * | 5/2006 | Lennon et al. | 504/206 |
| 7,291,213 B2 | 11/2007 | Ogawa et al. | |
| 7,442,682 B2 | 10/2008 | Kitaura et al. | |
| 7,709,158 B1 | 5/2010 | Schlaikjer et al. | |
| 2001/0014347 A1 | 8/2001 | Koike | |
| 2003/0158038 A1 | 8/2003 | Yanagihara et al. | |
| 2003/0211389 A1 | 11/2003 | Schlaikjer | |
| 2006/0034795 A1 | 2/2006 | Schmidt | |
| 2006/0065156 A1 | 3/2006 | Ogawa et al. | |
| 2007/0059940 A1 | 3/2007 | Islam et al. | |
| 2007/0161821 A1 | 7/2007 | Hall | |
| 2009/0221844 A1 | 9/2009 | Banavali et al. | |

FOREIGN PATENT DOCUMENTS

IN      156232 A1      6/1985
WO   2006128095 A2   11/2006

OTHER PUBLICATIONS

Database Accession No. 1987:63017, Dr. Bakel Izhar, "N-Phosphonomethylglycine Iminourea Derivatives," 1987, Abstract, Database CA (Online) Chemical Absttracts Service, Columbus, OH, XP002616886, 1 page.

* cited by examiner

*Primary Examiner* — Clinton Brooks
(74) *Attorney, Agent, or Firm* — Senniger Powers LLP; Joseph A. Schaper

(57) ABSTRACT

The present invention provides N-phosphonomethylglycine guanidine salts. The N-phosphonomethylglycine guanidine salts have improved herbicidal efficacy over glyphosate alone. The present invention also provides guanidine compounds and salts thereof.

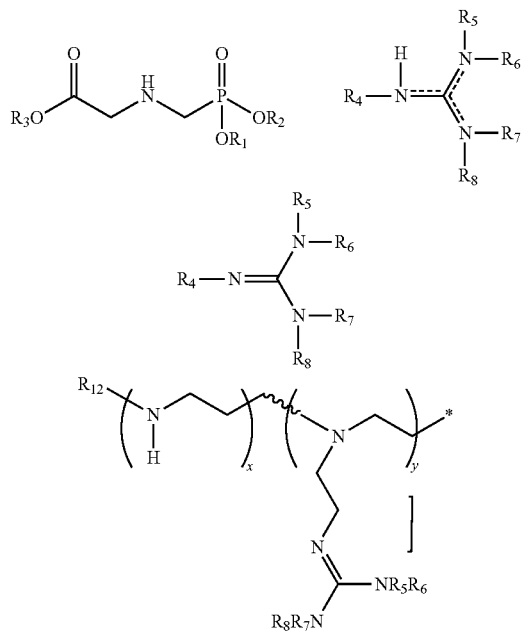

24 Claims, No Drawings

N-PHOSPHONOMETHYLGLYCINE GUANIDINE DERIVATIVE SALTS

REFERENCE TO RELATED APPLICATIONS

This application is the United States National Stage Application of International Application No. PCT/US2010/039745 filed Jun. 24, 2010, and claims the benefit of U.S. Provisional Application Ser. No. 61/221,819, filed Jun. 30, 2009, the entire disclosures of which are incorporated herein by reference.

BACKGROUND OF THE INVENTION

The present invention relates to N-phosphonomethylglycine guanidine derivative salts and herbicidal compositions including such salts.

N-phosphonomethylglycine (glyphosate) is well known as a highly effective, widely used and commercially effective herbicide useful for combating the presence of a wide variety of unwanted vegetation. Glyphosate in its strict sense is an acid compound, but the word "glyphosate" is used herein in a less restrictive sense to encompass not only glyphosate acid but also salts, adducts and esters thereof, and compounds of which are converted to glyphosate in plant tissues or which otherwise provide glyphosate ions. Glyphosate has three acid sites, and can therefore form tribasic salts. Monovalent glyphosate anions predominate at around pH 4. Divalent glyphosate anions predominate at about pH 7-8. Preferred aqueous compositions typically have a pH value not greater than about 8. At these pH values the fraction of glyphosate existing as a tribasic salt is negligibly small.

Glyphosate has low water solubility in free acid form, and is often formulated in commercial compositions in the form of a water soluble salt. Salts in commercial use include the ammonium salt, alkylamine salts, including the isopropylamine salts, alkali metal salts and the trimethyl sulfonium salts. Aminoguanidine salts of glyphosate are also common. Exemplary herbicidal salts of glyphosate are disclosed in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. In most of these salts, the counterion to the glyphosate anion is a relatively low molecular weight, non amphiphilic cation.

Many commercial formulations of glyphosate salts utilize these low molecular weight, non-amphiphilic salts. Commercial formulations of glyphosate salts containing the isopropylammonium salt include Roundup®, Accord®, and Roundup Ultra® herbicides, all commercially available from Monsanto Company. Commercial formulations of glyphosate containing the ammonium salt include Roundup® Dry and Rival® herbicides, both commercially available from Monsanto Company. Commercial formulations of glyphosate containing the sodium salt include Roundup® Geoforce herbicide of Monsanto Company, and commercial formulations containing the trimethylsulfonium salt include Touchdown® herbicide commercially available from Syngenta.

Salts of glyphosate possessing higher molecular weight, amphiphilic cations have also been disclosed. These amphiphilic cations include those having a hydrophilic moiety such as ammonium, ethanolammonium, polyoxyethylene ammonium, or sulfonium group, and a hydrophobic moiety containing between 1 to 4 hydrocarbyl groups having in total more than 6 carbon atoms. For example, U.S. Pat. No. 4,405,531 discloses primary, secondary, and tertiary ammonium salts of glyphosate possessing an amphiphilic cation having a molecular weight less than 300. U.S. Pat. No. 5,668,085 discloses a salt in which the cations of the glyphosate salt are derived from the surfactant. Specifically, U.S. Pat. No. 5,668,085 discloses ammonium salts of glyphosate with amphiphilic cations derived from polyoxyethylene tertiary C8-22 alkylamine surfactants. U.S. Pat. No. 5,668,085 discloses as an example N-cocoalkyl-N,N-diethanolammonium salt of glyphosate where "cocoalkyl" refers to a mixture of predominantly C12 and C14 alkyl chains, derived from coconut oil.

Glyphosate is usually applied to foliage together with amphiphilic materials, particularly surfactants. Surfactants enhance the biological effect of glyphosate in a number of ways, not all of which are completely understood. When glyphosate is applied to foliage as a dilute aqueous composition by conventional hydraulic spraying, the presence of surfactant in the aqueous composition can generally increase the percentage of smaller spray droplets and decrease the percentage of large spray droplets. Smaller droplets tend to have lower momentum than larger droplets and are more likely to be retained on a foliar surface and less likely to rebound from that surface. Spray retention is also facilitated by adhesion between surfactant molecules in a spray droplet and the foliar surface which is typically waxy and hydrophobic in most plants. This adhesion also aids in preventing the rebounding of droplets from the foliar surface and the run-off of droplets from the foliar surface. Surfactants also tend to increase the area of contact between a spray droplet and the foliar surface and thereby tend to enhance penetration of glyphosate from the droplet into and through the cuticles of leaves to access internal plant tissues.

The basicity possessed by guanidines and guanidine derivatives has contributed to their use in a wide variety of applications, ranging from cleaning products to additives in cosmetics.

SUMMARY OF THE INVENTION

The invention is directed to a salt of N-phosphonomethylglycine having the formula:

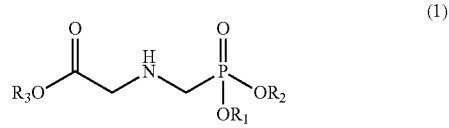

(1)

wherein $R_1$, $R_2$ and $R_3$ are independently hydrogen, sodium, potassium, ammonium, isopropylamine, n-propylamine, monoethanolamine, diethanolamine, dimethylamine, or a guanidine derivative having the formula:

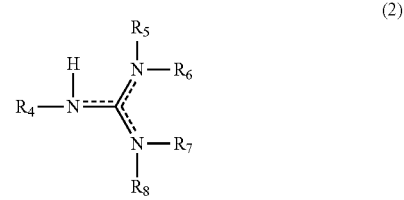

(2)

provided that at least one of $R_1$, $R_2$ and $R_3$ is the guanidine derivative;

$R_4$ is —$(CH_2)_m$—$(NR_9(CH_2)_n)_x$—$NR_{10}R_{11}$ or —$(CH_2)_m$—$CH(NH_2)CH(NH_2)R_{11}$, polyethyleneimino, $C_8$-$C_{30}$ alkyl, or $C_8$-$C_{30}$ alkenyl;

$R_5$, $R_6$, $R_2$ and $R_8$ are independently hydrogen or $C_1$-$C_5$ hydrocarbyl;

$R_9$ and $R_{10}$ are independently hydrogen or $C_1$-$C_5$ hydrocarbyl;

$R_{11}$ is $C_1$-$C_{30}$ hydrocarbyl; and m, n and x are independently an integer from 1 to 10. The N-phosphonomethylglycine guanidine derivative salts have improved herbicidal efficacy over glyphosate alone.

Another aspect of the invention is directed to an aqueous or solid herbicidal composition containing such a salt. In some instances, the aqueous herbicidal composition comprises such a salt of N-phosphonomethylglycine in an amount from about 1% to about 50% by weight of N-phosphonomethylglycine on an acid equivalent basis. In other embodiments, the solid herbicidal composition comprises such a salt of N-phosphonomethylglycine in an amount from about 10% to about 80% by weight of N-phosphonomethylglycine on an acid equivalent basis.

The present invention also provides a guanidine compound or a salt thereof having the formula:

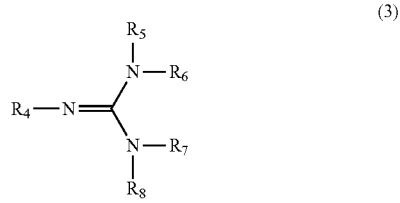

(3)

wherein $R_4$ is —$(CH_2)_m$—$(NR_9(CH_2)_n)_x$—$NR_{10}R_{11}$ or —$(CH_2)_m$—$CH(NH_2)CH(NH_2)R_{11}$ or polyethyleneimino; $R_5$, $R_6$, $R_7$ and $R_8$ are independently hydrogen or $C_1$-$C_5$ hydrocarbyl; $R_9$ and $R_{10}$ are independently hydrogen or $C_1$-$C_5$ hydrocarbyl; $R_{11}$ is $C_1$-$C_{30}$ hydrocarbyl; and m, n and x are independently an integer from 1 to 10.

Another aspect of the invention is directed to a guanidine compound or a salt thereof of formula (3) wherein $R_4$ is —$(CH_2)_m$—$(NR_9(CH_2)_n)_x$—$NR_{10}R_{11}$, —$(CH_2)_m$—$CH(NH_2)CH(NH_2)R_{11}$ or polyethyleneimino; $R_5$, $R_6$, $R_7$ and $R_8$ are independently hydrogen or $C_1$-$C_5$ hydrocarbyl; $R_9$ and $R_{10}$ are independently hydrogen or $C_1$-$C_5$ hydrocarbyl; $R_{11}$ is $C_1$-$C_{30}$ hydrocarbyl; and m, n and x are independently an integer from 1 to 10.

Still another aspect of the invention is directed to a guanidine compound or a salt thereof wherein $R_4$ is polyethyleneimino, the compound having the formula:

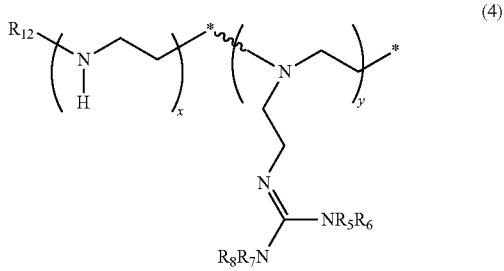

(4)

wherein $R_5$, $R_6$, $R_7$ and $R_8$ are independently hydrogen or $C_1$-$C_5$ hydrocarbyl, $R_{12}$ is hydrogen, $C_8$-$C_{30}$ alkyl, or $C_8$-$C_{30}$ alkenyl, and x and y are independently an integer from 2 to 20. In some embodiments, the compound is a block copolymer. In other embodiments, the compound is a random copolymer.

DETAILED DESCRIPTION

The invention provides herbicidal compositions comprising salts of N-phosphonomethylglycine having the formula (1) as shown above.

In some embodiments, $R_5$, $R_6$, $R_7$ and $R_8$ are independently hydrogen or $C_1$-$C_5$ hydrocarbyl, such as $C_1$-$C_4$ alkyl or $C_1$-$C_3$ alkyl. In some instances, $R_5$, $R_6$, $R_7$ and $R_8$ are each methyl. In other instances, $R_5$, $R_6$, $R_7$ and $R_8$ are each hydrogen.

In some embodiments, $R_4$ can be a $C_8$-$C_{30}$ alkyl or alkenyl group. Representative alkyl groups include octyl, nonyl, decyl, undecyl, dodecyl, tridecyl, tetradecyl, pentadecyl, hexadecyl, heptadecyl, octadecyl, coco, and tallow. Representative alkenyl groups include octenyl, nonenyl, decenyl, undecenyl, dodecenyl, tridecenyl, tetradecenyl, pentadecenyl, hexadecenyl, heptadecenyl, and octadecenyl. $R_4$ is preferably $C_{12}$-$C_{18}$ alkyl or $C_{12}$-$C_{18}$ alkenyl. In some instances, $R_4$ is preferably coco, tallow or hexadecyl. In other cases, $R_4$ is preferably dodecenyl, tetradecenyl, hexadecenyl or octadecenyl.

In some other embodiments, $R_4$ can be —$(CH_2)_m$—$(NR_9(CH_2)_n)_x$—$NR_{10}R_{11}$ or —$(CH_2)_m$—$CH(NH_2)CH(NH_2)R_{11}$ wherein $R_9$ and $R_{10}$ are independently hydrogen or $C_1$-$C_5$ hydrocarbyl; $R_{11}$ is $C_1$-$C_{30}$ hydrocarbyl; and m, n and x are independently an integer from 1 to 10. In some cases, $R_4$ is —$(CH_2)_m$—$CH(NH_2)CH(NH_2)R_{11}$, m is 1 and $R_{11}$ is a $C_8$-$C_{30}$ alkyl or alkenyl group such as those listed above. In some embodiments, $R_4$ is —$(CH_2)_m$—$(NR_9(CH_2)_n)_x$—$NR_{10}R_{11}$, $R_9$ and $R_{10}$ are hydrogen, $R_{11}$ is a $C_8$-$C_{30}$ alkyl or $C_8$-$C_{30}$ alkenyl group such as those listed above, m and n are 2, and x is an integer from 1 to 5.

In other embodiments, $R_4$ can be polyethyleneimino (PEI) and the guanidine compound is a block copolymer or a random copolymer having from 4 to 40 constituent monomer units. In some embodiments, $R_5$, $R_6$, $R_7$ and $R_8$ are independently hydrogen or $C_1$-$C_5$ hydrocarbyl. In some cases $R_5$, $R_6$, $R_7$ and $R_8$ are methyl and in other cases $R_5$, $R_6$, $R_7$ and $R_8$ are hydrogen.

In some other embodiments, $R_4$ can be —$(CH_2)_m$—$(NR_9(CH_2)_n)_x$—$NR_{10}R_{11}$, —$(CH_2)_m$—$CH(NH_2)CH(NH_2)R_{11}$ or PEI, as defined above.

In some embodiments, the N-phosphonomethylglycine guanidine derivative salts are dispersed or dissolved in a liquid carrier to form a herbicidal composition. The liquid carrier is preferably aqueous. More preferably, the liquid carrier is water or deionized water. The N-phosphonomethylglycine guanidine derivative salts can be present in solution as monobasic salts, dibasic salts and tribasic salts. Monobasic salts as used herein refer to salts in which there is one protonated guanidine derivative for every glyphosate anion. Dibasic salts as used herein refer to salts in which there are two protonated guanidine derivatives for every glyphosate dianion. Tribasic salts as used herein refer to salts in which there are three protonated guanidine derivatives for every glyphosate trianion. Preferably, the N-phosphonomethylglycine guanidine derivative salts are present in the liquid carrier as monobasic salts and/or dibasic salts.

In the herbicidal compositions of the invention the mole ratio of guanidine derivative to glyphosate ranges from between about 3.5:1 to about 1:1. Preferably, the mole ratio of guanidine derivative to glyphosate is about 1:1.

The present invention also provides guanidine compounds of the formula (3), wherein $R_4$-$R_{11}$, m, n and x are as defined above with regard to the salts of formula (1).

Guanidine compounds of the formula (4) are also provided wherein $R_5$-$R_8$ are as defined above with regard to the salts of formula (1). $R_{12}$ is hydrogen, $C_8$-$C_{30}$ alkyl, or $C_8$-$C_{30}$ alkenyl. Representative alkyl groups include octyl, nonyl, decyl, undecyl, dodecyl, tridecyl, tetradecyl, pentadecyl, hexadecyl, heptadecyl, octadecyl, coco, and tallow. Representative alkenyl groups include octenyl, nonenyl, decenyl, undecenyl, dodecenyl, tridecenyl, tetradecenyl, pentadecenyl, hexadecenyl, heptadecenyl, and octadecenyl. $R_{12}$ is preferably $C_{12}$-$C_{18}$ alkyl or $C_{12}$-$C_{18}$ alkenyl. In some instances, $R_{12}$ is preferably coco, tallow or hexadecyl. In other cases, $R_{12}$ is preferably dodecenyl, tetradecenyl, hexadecenyl or octadecenyl. In formula (4), x and y are independently an integer from 2 to 20. In some instances, the compound of formula (4) has a weight average molecular weight from about 500 to about 7,000, preferably from about 1,000 to about 3,000. In some embodiments, the compound is a block copolymer. In other embodiments, the compound is a random copolymer.

The guanidine compounds can also be made into salts through the use of an acid, for example. An acid for forming salts of the guanidine compounds may be either an organic acid or an inorganic acid. Examples thereof include monocarboxylic acids such as formic acid, acetic acid, propionic acid, butyric acid, isobutyric acid, hexanoic acid, heptanoic acid, octanoic acid, nonanoic acid, decanoic acid, lauric acid, myristic acid, palmitic acid, stearic acid, acrylic acid, methacrylic acid, crotonic acid, isocrotonic acid, phenylacetic acid, cinnamic acid, benzoic acid, sorbic acid, nicotinic acid, urocanic acid and pyrrolidone-carboxylic acid; dicarboxylic acids such as oxalic acid, malonic acid, succinic acid, glutamic acid, adipic acid, pimelic acid, cork acid, azelaic acid, sebacic acid, maleic acid, fumaric acid, phthalic acid and terephthalic acid; hydroxy acids such as glycolic acid, lactic acid, malic acid, tartaric acid, citric acid and hydroxybenzoic acid; amino acids such as glycine, alanine, β-alanine, valine, leucine, phenylalanine, tyrosine, serine, threonine, methionine, cysteine, cystine, proline, hydroxyproline, pipecolic acid, tryptophan, aspartic acid, asparagine, glutamic acid, glutamine, lysine, histidine, ornithine, arginine and aminobenzoic acid; lower alkylsulfonic acids such as methanesulfonic acid and trifluoromethanesulfonic acid; arylsulfonic acids such as benzenesulfonic acid and p-toluenesulfonic acid; hydrohalogenic acids such as hydrofluoric acid, hydrochloric acid, hydrobromic acid and hydroiodic acid; and inorganic acids such as perchloric acid, sulfuric acid, nitric acacia, phosphoric acid and carbonic acid.

Specific examples of some preferred guanidine compounds for use in the invention include, but are not limited to:

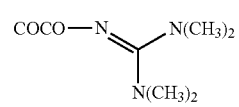

(5)

N,N,N,N-tetramethyl-(coco)guanidine

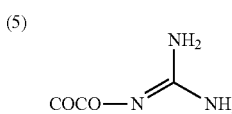

(6)

2-cocoguanidine

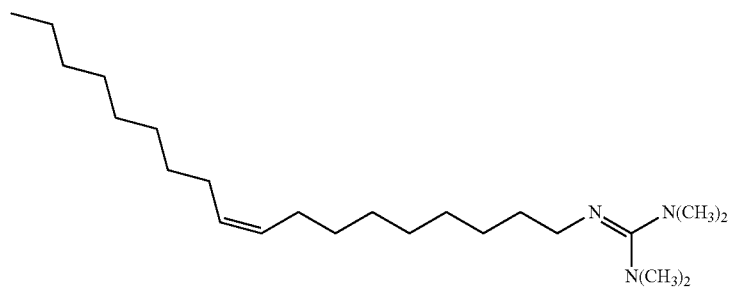

(7)

(Z)-1,1,3,3-tetramethyl-2-(octadec-9-enyl)guanidine

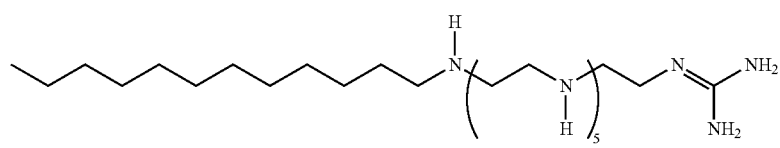

(8)

2-3,6,9,12,15,18-hexaazatriacontyl guanidine

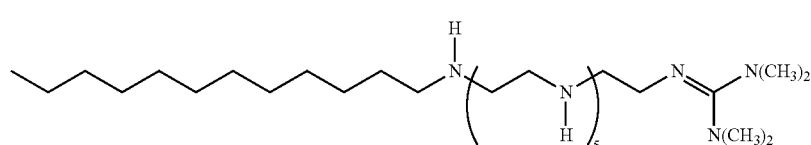

(9)

1,1,3,3,-tetramethyl-2-3,6,9,12,15,18-hexaazatriacontyl guanidine

-continued

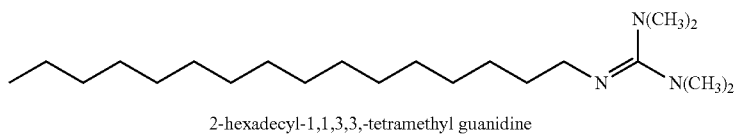

2-hexadecyl-1,1,3,3,-tetramethyl guanidine (10)

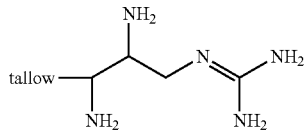

2-(2,3-diaminopropyl)tallow guanidine (11)

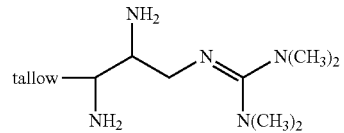

2-(2,3-diaminopropyl)tallow-1,1,3,3-tetramethyl guanidine (12)

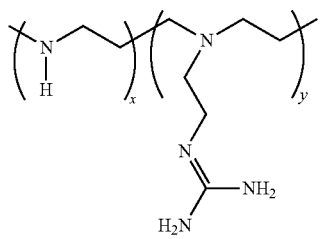

PEI 1800 guanidine (13)

wherein x and y are selected such that the polymeric portion of the compound (i.e., the x and y units) possesses a molecular weight of 1800.

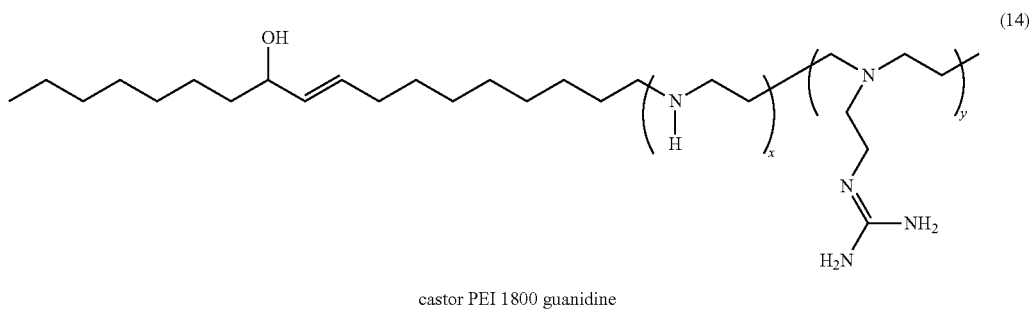

castor PEI 1800 guanidine (14)

wherein x and y are selected such that the polymeric portion of the compound (i.e., the x and y units) possesses a molecular weight of 1800.

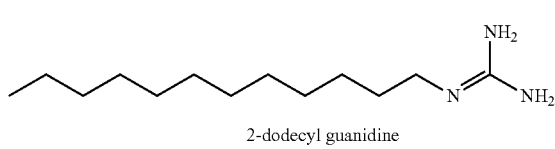

2-dodecyl guanidine (15)

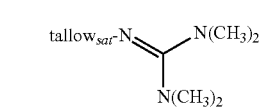

N,N,N-tetramethyl-(tallow$_{sat}$) guanidine (16)

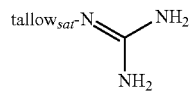

tallow$_{sat}$ guanidine (17)

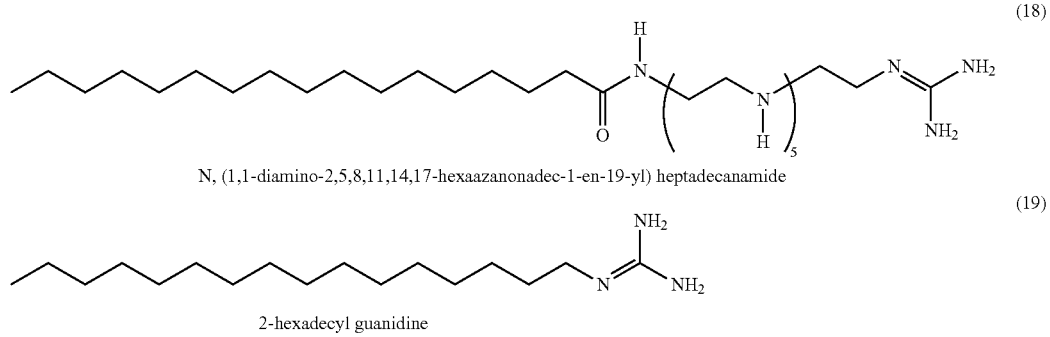

N, (1,1-diamino-2,5,8,11,14,17-hexaazanonadec-1-en-19-yl) heptadecanamide (18)

2-hexadecyl guanidine (19)

In some embodiments, the present invention is directed to aqueous herbicidal compositions comprising a guanidine salt of N-phosphonomethylglycine, as described above, in an amount from about 1% to about 50% by weight of N-phosphonomethylglycine on an acid equivalent basis. In other embodiments, the present invention is directed to solid herbicidal compositions comprising a guanidine salt of N-phosphonomethylglycine, as described above, in an amount from about 10% to about 80% by weight of N-phosphonomethylglycine on an acid equivalent basis.

The present invention is further directed to aqueous herbicidal concentrates. The concentration of the glyphosate component in an aqueous herbicidal concentrate according to the present invention is typically at least about 300 grams acid equivalent per liter ("g a.e./L"), such as at least about 360 g a.e./L, such as at least about 390 g a.e./L. In preferred compositions of the invention, glyphosate concentration is not lower than 400 g a.e./L or about 420 g a.e./L, in particularly preferred compositions not lower than about 480 g a.e./L, or even about 540 g a.e./L, for example about 480 to about 540 g a.e./L, or about 480 to about 600 g a.e./L, or more. Accordingly, the concentration of the glyphosate component in a herbicidal concentrate is typically between about 300 g a.e./L and about 600 g a.e./L, preferably between about 420 g a.e./L and about 600 g a.e./L, even more preferably between about 480 g a.e./L and about 540 g a.e./L.

The present invention is still further directed to ready to use (RTU) formulations are prepared by diluting herbicidal concentrates with appropriate amounts of water. The concentration of the glyphosate component in aqueous RTU compositions of the present invention is typically at least about 1 g a.e./L, and generally from about 1 g a.e./L to about 50 g a.e./L. In order to provide more economical RTU formulations providing prolonged herbicidal activity, the concentration of the glyphosate component in the RTU composition is more preferably from about 5 g a.e./L to about 20 g a.e./L.

The pH of the herbicidal composition of the present invention is a factor in stability, cloud point, compatibilization of glyphosate salts with any surfactants used, and compatibilization with co-herbicides, if added. In this regard, the pH of a herbicidal composition comprising potassium glyphosate, for example, as its predominant glyphosate component may be from about 4 to about 8, such as from about 4.5 to about 5.5. In other embodiments, the pH of a herbicidal composition comprising diammonium glyphosate as its predominant glyphosate component may be from about 4 to about 8, such as from about 5 to about 7, such as from about 5.5 to about 6.5. Agents for acidic pH adjustment include mineral acids such as, for example, hydrochloric acid, nitric acid or sulfuric acid, and organic acids such as, for example, acetic acid or dicarboxylic acids. Agents for alkaline pH adjustment include, for example, sodium hydroxide, potassium hydroxide, ammonia, and organic bases, such as IPA, MPA, and DMA.

The herbicidal compositions, i.e., liquid concentrates and ready to use formulations, may further comprise a co-herbicide. In some embodiments, water-soluble co-herbicides can be included in the compositions of the present invention. Water-soluble co-herbicides include acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

In some embodiments, co-herbicides that are not readily water-soluble can be coupled into the aqueous herbicidal composition by inclusion of a sufficient quantity of an appropriate surfactant. In addition, the compositions of the present invention may include finely-divided, water-insoluble herbicides. Examples of herbicides having limited water solubility include, for example, acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluoroxypyr-1-methylheptyl, flurtamone, fluthiacet-methyl, fomesafen, halosulfuron, haloxyfop-methyl, hexazinone, imazamox, imazosulfuron, indanofan, isoproturon, isouron, isoxaben, isoxaflutole, isoxapyrifop, lactofen, lenacil, linuron, mefenacet, mesotrione, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate. Additional herbicidal active ingredient(s) in a concentrate or RTU formulation are present in an agriculturally useful concentration that will vary depending on the particular additional herbicide(s) selected for inclusion and is readily determined by those skilled in the art.

The herbicidal compositions may further comprise other conventional adjuvants, excipients, or additives known to those skilled in the art. These other additives or ingredients may be introduced into the compositions of the present invention to provide or improve certain desired properties or characteristics of the formulated product. Hence, the herbicidal composition may further comprise one or more additional ingredients selected from, without limitation, foam-moderating agents, surfactants, preservatives or anti-microbials, antifreeze agents, solubility-enhancing agents, dyes, pH adjusters and thickening agents.

Suitable surfactants are known to those skilled in the art and include cationic, nonionic, and anionic surfactants. Additional surfactants may be included so long as they do not adversely affect the stability or compatibility of the guanidine component with the remainder of the glyphosate formulation.

Suitable classes of cationic surfactants include primary, secondary and tertiary alkylamines, primary, secondary and tertiary alkylaminium salts in which an amine group is substantially protonated in the formulation, onium salts such as quaternary alkylammonium salts, and mixtures thereof. A wide variety of primary, secondary, tertiary, quaternary and zwitterionic alkylamine and alkylammonium salt surfactants can be utilized in the practice of the present invention. A subclasses of primary, secondary and tertiary alkylamine surfactants for use in the present invention are alkyl amine oxides, alkyletheramines, and alkyletheramine oxides as disclosed in U.S. Pat. No. 5,750,468 (to Wright). Preferred subclasses of zwitterionic or amphoteric alkylammonium salts for use in the present invention are amino acid derivatives such as alkyl, dialkyl or alkyl lower-alkyl glycines, beta-alanines, aspartates, and the like. Preferred alkylammonium salts are quaternary alkylammonium salts. Classes of quaternary alkylammonium salts useful in the present invention include quaternized (e.g., N-methyl) alkylamines, quaternized polyoxyalkylene alkylamines, quaternary salts of pyridines, quaternary salts of carboxylated imidazolines (open and closed chain) and trialkyl betaines. Trialkylamine oxides are a class of compounds which form quaternary ammonium hydroxide salts upon addition to water and are also useful in the practice of the present invention. Other general classes of quaternary alkylammonium and alkylaminium salt surfactants useful in the practice of the present invention will be known to and readily ascertainable by those skilled in the art.

Nonionic surfactants suitable for the practice of the present invention include, without restriction, polyoxyalkylene primary and secondary $C_{8-20}$ alkylethers, alkoxylated acetylenic diols, polyoxyalkylene mono- and di($C_{8-20}$ alkyl)phenylethers, polyoxyalkylene di- and tristyrylphenylethers, polyoxyalkylene $C_{8-20}$ fatty acid esters, polyoxyalkylene $C_{8-20}$ alcohols, alkoxylated vegetable oils, alkoxylated castor oil, block copolymers of ethylene oxide and propylene oxide and $C_{2-6}$ alkyl adducts thereof, glycerol fatty acid esters, sorbitan $C_{8-20}$ mono-, di- and tri($C_{8-20}$ fatty acid) esters, polyoxyalkylene sorbitan mono-, di- and tri($C_{8-20}$ fatty acid) esters, sucrose esters and $C_{8-20}$ alkyl polyglycosides.

Anionic surfactants useful as components of the stabilizing system of compositions of the include, without restriction, $C_{8-20}$ alkyl carboxylates including fatty acids, $C_{8-20}$ alcohol sulfates, $C_{8-20}$ alcohol phosphate mono- and diesters, $C_{8-20}$ alcohol and ($C_{8-20}$ alkyl)phenol polyoxyethylene ether carboxylates, sulfates and sulfonates, $C_{8-20}$ alcohol and ($C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, $C_{8-20}$ alkyl polyoxyethylene sulfosuccinates and sulfosuccinamates, and $C_{8-20}$ acyl glutamates, sarcosinates, isethionates and taurates.

Suitable foam-moderating agents include silicone-based compositions. An example of a foam-moderating agent for compositions is SAG-10, available from GE Silicones Corporation (Wilton, Conn.). The amount of foam-moderating agent optionally employed is that which is sufficient to inhibit and/or reduce an amount of foam that may otherwise be formed during the process of preparing and containerizing the formulation and/or use thereof to a desired and satisfactory level. Generally, the concentration of foam-moderating agent is in the range from about 0.001% up to about 0.05% by weight of the composition, and typically from about 0.01% to about 0.03% by weight of the composition, although greater or lesser amounts may be employed.

The compositions may also comprise a preservative such as PROXEL GXL containing 1,2-benzisothiazolin-3-one (CAS No. 2634-33-5) available from Avecia, Inc. (Wilmington, Del.), DOWICIL 150 containing cis-1-(3-chloroallyl)-3, 5,7-triaza-1-azoniaadmatane chloride (CAS No. 051229-78-8) available from Dow Chemical Company (Midland, Mich.), NIPACIDE BIT20DPG containing benzisothiazolinone available from Clariant Corporation (Greensboro, N.C.), LEGEND MK anti-microbial biocide available from Rohm and Haas Co. (Philadelphia, Pa.), sorbic acid, mixtures thereof and the like in the range of from about 0.01% to about 0.2% by weight, preferably about 0.1% by weight of the composition.

Suitable antifreeze agents include ethylene glycol and propylene glycol and generally may be present at a concentration of from about 0.1% to about 10% by weight of the RTU composition. Antifreeze agents assist in lowering the freezing point of aqueous solutions and maintaining solubility of the components of the composition such that components do not crystallize or precipitate during cycles of freezing and thawing.

Although the compositions of the present invention generally show good overall stability and viscosity properties without the addition of any further additives, the addition of a solubility-enhancing agent (also commonly referred to as a cloud point enhancer or stabilizer) may significantly improve the properties of the formulations. Solubility-enhancing agents include polymer derivatives of ethylene glycol and propylene glycol (e.g., 200-1200 average molecular weight), glycerol, sugars, mixtures thereof and the like in amounts up to about 10%, preferably from about 0.05 to about 10% by weight, more preferably from about 0.1 to about 1% by weight of the RTU composition.

A guanidine compound of formula (3) can be prepared by combining the required amounts of a urea compound, solvent, phosphorous oxychloride, and an amine compound, with mixing using a mechanical stirrer or any other suitable container or device producing the necessary amount of agitation or circulation to thoroughly mix the ingredients. The order of addition of the starting materials is not narrowly critical to the stability of the reaction mixture. In various embodiments, the reaction mixture is prepared according to an order of component addition. Herein, solvent is preferably added to the mixing vessel first, followed by the addition of the urea compound and phosphorous oxychloride. Next, the amine compound is added. Preferably, the components are combined at room temperature. The agitation continues for a period of time ranging from a few hours to a day, preferably for several hours. Preferably, the agitation is done at room temperature.

After the initial reaction mixture is formed from the urea compound, phosphorous oxychloride, solvent and the amine compound, a base is added slowly while maintaining the temperature of the reaction mixture, preferably at room temperature. After the reaction, the mixture is cooled to form an emulsion, and a solvent is added to break the emulsion. After separation of the aqueous phase, the organic phase is washed with water. The organic phase is then dried. The solution is filtered, and the solvent is evaporated. The resulting residue is filtered. The filtrate solution is concentrated and the resulting guanidine compound is dried overnight under vacuum.

The urea compound is preferably an alkylurea such as tetramethylurea. The amine compound is preferably an alkylamine or a polyalkylene amine. Representative examples include, but are not limited to, cocoamine, oleylamine, hexadecylamine, tallowamine, polyethylene amine, castor oil derived polyethylene amine, 3,6,9,12,15,18-hexaazatriacontylamine, and dodecylamine.

Another method for preparing a guanidine compound of formula (3) comprises combining the required amounts of cyanamide, solvent, and an amine compound, with mixing using a mechanical stirrer or any other suitable container or device producing the necessary amount of agitation or circulation to thoroughly mix the ingredients. The order of addition of the starting materials is not narrowly critical to the stability of the reaction mixture. In various embodiments, the reaction mixture is prepared according to an order of component addition. Herein, solvent is preferably added to the mixing vessel first, followed by the addition of the cyanamide. Next, the amine compound is mixed with solvent and added to the cyanamide solution. Preferably, the components are combined at room temperature. The agitation continues for a period of time ranging from a few minutes to several hours, preferably for a few hours. Preferably, the agitation is done at an elevated temperature, preferably about 50° C., and then the solvent is evaporated. The residue is dissolved in a solution comprising a solvent, a base and water. This mixture is stirred for a few minutes to several hours, preferably for about an hour, at an elevated temperature. After separation of the aqueous phase, the organic phase is dried. The solution is filtered, and the solvent is evaporated. The resulting guanidine is dried overnight under vacuum.

The herbicidal compositions of the present invention may be prepared by combining the required amounts of glyphosate, water, and guanidine compound, with mixing using a mechanical stirrer or any other suitable container or device producing the necessary amount of agitation or circulation to thoroughly mix the ingredients. The order of addition of the starting materials is not narrowly critical to the stability of the final composition. In various embodiments, the herbicidal composition is prepared according to an order of component addition. Herein, water is preferably added to the mixing vessel first, followed by the addition of the glyphosate salt. Next, the guanidine compound is added, followed by the addition of any optional additives. Preferably, the guanidine compound is combined with the source of glyphosate anions at room temperature. The agitation continues for a period of time ranging from a few minutes to several hours, preferably for about one hour. Preferably, the agitation is done at room temperature.

Preferably, the liquid medium is an aqueous medium. Even more preferably, the liquid medium is deionized water. The source of glyphosate anions include glyphosate salts such as, for example, monobasic, dibasic, or tribasic salts and organic amines, alkali metal, alkaline earth metal, ammonium (e.g., monoammonium, diammonium, or triammonium) or sulfonium (e.g., monosulfonium, disulfonium, or trimethylsulfonium ("TMS") salts of glyphosate. The organic amine salts can comprise aliphatic or aromatic amine salts and can include primary, secondary, tertiary, or quaternary amine salts. Specific representative examples of such organic amine salts include isopropylammonium ("IPA"), n-propylammonium, ethylammonium, dimethylammonium ("DMA"), monoethanolammonium ("MEA"), ethylenediamine and hexamethylenediamine salts of glyphosate. Specific representative examples of alkali metal salts include potassium and sodium salts of glyphosate. Preferably, the source of glyphosate anions is glyphosate acid, or a sodium, potassium, ammonium, isopropylamine, n-propylamine, monoethanolamine, diethanolamine, or dimethylamine salt of glyphosate.

The RTU compositions of the present invention can be prepared by diluting an aqueous herbicidal concentrate with an appropriate amount of water.

The present invention is also directed to a method for killing or controlling weeds or other unwanted plants by spraying or otherwise applying a herbicidally effective amount of the RTU or diluted concentrate formulations described herein to the foliage of the plants to be treated. The herbicidal spray compositions included in the present invention can be applied to the foliage of the plants to be treated through any of the appropriate methods that are well known to those having skill in the art. In one embodiment, the RTU composition is packaged in a portable container suitable for hand carry by the user and fitted with an apparatus for manually releasing the composition from the container onto the foliage of the plants to be treated in the form of a spray.

The compositions of the present invention can be used to kill or control the growth of a wide variety of plants. Particularly important annual dicotyledonous plant species include, without limitation, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), Russian thistle (*Salsola* spp.), sida (*Sida* spp.), wild mustard (*Sinapis arvensis*) and cocklebur (*Xanthium* spp.).

Particularly important annual monocotyledonous plant species that may be killed or controlled using the compositions of the present invention include, without limitation, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial dicotyledonous plant species for control of which a composition of the invention can be used include, without limitation, mugwort (*Artemisia* spp.), milkweed (*Asclepias* spp.), Canada thistle (*Cirsium arvense*), field bindweed (*Convolvulus arvensis*) and kudzu (*Pueraria* spp.).

Particularly important perennial monocotyledonous plant species for control of which a composition of the invention can be used include, without limitation, brachiaria (*Brachiaria* spp.), bermudagrass (*Cynodon dactylon*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial plant species for control of which a composition of the invention can be used include, without limitation, horsetail (*Equisetum* spp.), bracken (*Pteridium aquilinum*), blackberry (*Rubus* spp.) and gorse (*Ulex europaeus*).

Suitable herbicidally efficacious application or spray rates used in the practice of the present invention will vary depending on the particular composition and concentration of active ingredients, the desired effects, plant species treated, weather and other factors. What constitutes a "desired effect" varies according to the standards and practice of those who investigate, develop, market and use compositions and the selection of application rates that are herbicidally effective for a composition of the invention is within the skill of those skilled in the art.

Thus, glyphosate compositions of the present invention, and a process for treating plants with such compositions, can be useful on any of the above species. In a particular contemplated process, a plant treatment composition of the invention comprising one or more amphiphilic glyphosate salt(s) is applied to foliage of crop plants genetically transformed to tolerate glyphosate, and simultaneously to foliage of weeds or undesired plants growing in close proximity to such crop plants. This process results in control of the weeds or undesired plants while leaving the crop plants substantially unharmed. Crop plants genetically transformed to tolerate glyphosate include those whose seeds are sold by Monsanto or under license from Monsanto bearing the Roundup Ready® trademark. These include varieties of cotton, soybean, canola and corn.

Application of plant treatment compositions to foliage of plants is preferably accomplished by spraying liquids, such as spray nozzles, atomizers, or the like. Compositions of the present invention can be used in precision farming techniques, in which apparatus is employed to vary the amount of exogenous chemical substance applied to different parts of a field, depending on variables such as the particular plant species present, soil composition, and the like. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

The guanidine compounds of the present invention can be utilized as detergents or protein denaturants, or in the cosmetic field. Use in the cosmetic field includes incorporation into cosmetics such as shampoos and skin care products. The guanidine compounds themselves could be used as emollients in cosmetics. The guanidine compounds of the present invention can also be formulated for use in body hygiene compositions such as deodorants and antiperspirants. The guanidine compounds can also be formulated for use in compositions for the hair, such as shampoos, conditioners, and dying and styling products. The guanidine compounds of the present invention could also be used as surfactants in cosmetics, shampoos and skin care products.

DEFINITIONS

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The term "halogen" as used herein alone or as part of another group refer to chlorine, bromine, fluorine, and iodine.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

As used herein "coco" is intended to mean hydrocarbyl moieties derived from the coconut oil plant, typically $C_{12}$ hydrocarbyl moieties. "Tallow" is intended to mean hydrocarbyl moieties derived from beef tallow or other animal fat, typically possessing $C_{12}$-$C_{18}$ hydrocarbyl moieties. "Castor PEI1800" is intended to mean a polyethylene imine with a hydrophobic portion derived from castor oil. "PEG 400" is intended to mean a polyethylene glycol possessing an average molecular weight of 400.

"Herbicidal effectiveness" as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

Having described the invention in detail, it will be apparent that modifications and variations are possible without departing from the scope of the invention defined in the appended claims.

EXAMPLES

The following examples are provided for illustrative purposes only and are not intended to limit the scope of the present invention.

Example 1

Preparation of N,N,N,N-tetramethyl-(coco)guanidine (Compound 5)

72.5 g tetramethylurea (0.65 mol, 116 g/mol) and 99.4 g phosphorous oxychloride (0.65 mol, 153.3 g/mol) were added to 400 ml toluene. The reaction mixture was stirred for 8 hours at room temperature. To the resulting solution was added, by injection over a sufficiently long period of time to keep the temperature at 25° C., 60 g cocoamine (0.325 mol, 185 g/mol, Genamine™ 6160). The reaction mixture was stirred for 14 hours at room temperature. 300 ml sodium hydroxide solution 10 mol/l (3 mol) was added slowly to maintain the temperature at 25° C. The reaction mixture was cooled to 25° C. The emulsion was broken by the addition of 50 ml ethanol. After separation of the aqueous phase, the organic phase was washed with 200 ml water. The organic phase was then dried over sodium hydroxide pellets. The solution was filtered, and the solvent was evaporated. The resulting residue was filtered over aluminum oxide pellets using isopropyl ether. The filtrate solution was concentrated and the resulting N,N,N,N-tetramethyl-(coco)guanidine was dried overnight under vacuum. The dried residue weighed 46 g and the yield was around 47%.

Formulation of N,N,N,N-tetramethyl-(coco)guanidine with glyphosate acid (Formulation 1A)

A composition of the invention was prepared by the following procedure. Into a 500 ml screw capped vial were introduced 29.4 g N,N,N,N-tetramethyl-(coco)guanidine (synthesized as above) and 12.2 g glyphosate acid, purity 98.5%. Deionized water in an amount of 198.8 g was added to provide an aqueous medium for neutralization of the glyphosate acid with the N,N,N,N-tetramethyl-(coco)guanidine. The mixture was stirred at room temperature for one hour to produce a homogeneous composition which had a glyphosate a.e. concentration of 5.0% by weight. Upon dilution to glyphosate a.e. concentration of 0.5% by weight, pH was found to be 4.7. At this concentration, supramolecular aggregates were observed having a mean diameter of 160 nm, and the surface tension was 34 mN/m. The calculated mole ratio of protonatable guanidine groups to glyphosate was 1.39:1.

Example 2

Preparation of N,N,N,N-tetramethyl-(tallow$_{sat}$) guanidine (Compound 16)

118 g phosphorous oxychloride (0.771 mol, 153.3 g/mol) was added to a solution of 100 g tallow$_{sat}$ amine (0.386 mol, 280 g/mol, Noram™ SH, CECA) in 200 ml toluene under nitrogen. The reaction mixture was stirred for 24 hours at room temperature. To the resulting solution was added, by injection over a sufficiently long period of time to keep the temperature at 25° C., 89.6 g tetramethylurea (0.771 mol, 116 g/mol) in solution with 300 ml toluene. The reaction mixture was stirred for 24 hours at room temperature. The reaction mixture was poured on 400 g ice. 450 ml sodium hydroxide solution 10 mol/l (3 mol) was added slowly to maintain the temperature at under 25° C. The reaction mixture was stirred for 4 hours at 50° C. The reaction mixture was cooled to 25° C. The emulsion was broken by the addition of 100 ml ethanol. After separation of the aqueous phase, the organic phase was washed with 400 ml water. Finally, the organic phase was dried over sodium hydroxide pellets. The solution was filtrated, and the solvent was evaporated. The resulting N,N,N,N-tetramethyl-(tallow$_{sat}$)guanidine was dried overnight under vacuum. The dried residue weighed 99 g and the yield was around 67%.

Formulation of N,N,N,N-tetramethyl-(tallow$_{sat}$) guanidine with glyphosate acid (Formulation 2A)

A composition of the invention was prepared by the following procedure. Into a 500 ml screw capped vial were introduced 22.9 g N,N,N,N-tetramethyl-(tallow$_{sat}$)guanidine (synthesized as above) and 12.2 g glyphosate acid, purity 98.5%. Deionized water in an amount of 208.3 g was added to provide an aqueous medium for neutralization of the glyphosate acid with the N,N,N,N-tetramethyl-(tallow$_{sat}$)guanidine. The mixture was stirred at room temperature for one hour to produce a homogeneous composition having a glyphosate a.e. concentration of 5.0% by weight. Upon dilution to glyphosate a.e. concentration of 0.5% by weight, pH was found to be 4.6. The calculated mole ratio of protonatable guanidine groups to glyphosate was 0.85:1.

Example 3

Preparation of 2-cocoguanidine (Compound 6)

A solution of 100 g cocoamine (0.46 mol, 217 g/mol, Radiamine 6160, Fina) in 150 ml ethanol was added to a solution of cyanamide (0.588 mol, 42 g/mol) in 400 ml ethanol under nitrogen. During the addition, the temperature was maintained at a temperature under 25° C. The reaction mixture was stirred for 24 hours at 50° C., and then the ethanol was completely evaporated. The residue was dissolved in a solution of 400 ml isopropyl ether, 100 ml sodium hydroxide 10 mol/l and 100 ml water. The reaction mixture was stirred for 1 hour at 50° C. After separation of the aqueous phase, the organic phase was dried over sodium hydroxide pellets for 1 hour at a temperature of 50° C. The solution was filtrated, and the solvent was evaporated. The resulting 2-cocoguanidine was dried overnight under vacuum. The dried residue weighed 103 g, and the yield was around 85%.

Formulation of 2-cocoguanidine with glyphosate acid (Formulation 3A)

A composition of the invention was prepared by the following procedure. Into a 500 ml screw capped vial were introduced 20.4 g 2-cocoguanidine (synthesized as above) and 10.2 g glyphosate acid, purity 98.5%. Deionized water in an amount of 169.4 was added to provide an aqueous medium for neutralization of the glyphosate acid with the 2-cocoguanidine. The mixture was stirred at room temperature for one hour to produce a homogeneous composition having a glyphosate a.e. concentration of 5.0% by weight. Upon dilution to glyphosate a.e. concentration of 0.5% by weight, pH was found to be 4.6. The calculated mole ratio of protonatable guanidine groups to glyphosate was 1.3:1.

Example 4

Preparation of PEI1800-guanidine (Compound 13)

3.63 g cyanamide (0.086 mol, 42 g/mol) was added to a solution of 15.5 g PEI1800 (polyethylene amine of molecular weight 1800) (0.0086 mol, 1800 g/mol, Aldrich) with 15.5 g water. The reaction mixture was stirred for 3 hours at 100° C., and then the water was completely evaporated. The residue PEI1800-guanidine was dried overnight under vacuum. The dried residue weighed 16 g, and the yield was around 84%.

Formulation of PEI1800-guanidine with glyphosate acid (Formulation 4A)

A composition of the invention was prepared by the following procedure. Into a 500 ml screw capped vial were introduced 9 g PEI1800-guanidine synthesized as above and 12.2 g glyphosate acid, purity 98.5%. Deionized water in an amount of 218.8 g was added to provide an aqueous medium for neutralization of the glyphosate acid with the PEI1800-guanidine. The mixture was stirred at room temperature for one hour to produce a homogeneous composition having a glyphosate a.e. concentration of 5.0% by weight. Upon dilution to glyphosate a.e. concentration of 0.5% by weight, pH was found to be 4.5. At this concentration, supramolecular aggregates were observed having a mean diameter of 5 nm and 160 nm, and the surface tension was 60.5 mN/m. The calculated mole ratio of protonatable guanidine groups to glyphosate was 2.68:1.

Example 5

Preparation of castor PEI1800-guanidine (Compound 14)

20.5 g cyanamide (0.488 mol, 42 g/mol) was added to a solution of 51.7 g castor PEI1800 (castor oil derived polyethylene amine) (0.0245 mol, 2111 g/mol, Aldrich) with 200 ml toluene. The reaction mixture was stirred for 4 hours at 80° C. then 2 hours at 100° C. 100 ml ethanol and 100 ml water were added to the reaction mixture. After separation of the aqueous phase, the organic phase was washed again with 100 ml water. The organic phase was dried over $MgSO_4$. The solution was filtrated, and the solvent was evaporated. The resulting castor PEI1800-guanidine was dried overnight under vacuum. The dried residue weighed 58 g, and the yield was around 93%.

Formulation of castor PEI1800-guanidine with glyphosate acid (Formulation 5A)

A composition of the invention was prepared by the following procedure. Into a 500 ml screw capped vial were introduced 15.1 g castor PEI1800-guanidine synthesized as above and 12.2 g glyphosate acid, purity 98.5%. Deionized water in an amount of 212.7 g was added to provide an aqueous medium for neutralization of the glyphosate acid with the castor PEI1800-guanidine. The mixture was stirred at room temperature for one hour to produce a homogeneous composition having a glyphosate a.e. concentration of 5.0% by weight. Upon dilution to glyphosate a.e. concentration of 0.5% by weight, pH was found to be 4.7. At this concentration, supramolecular aggregates were observed having a mean diameter of 6 nm, and the surface tension was 44.9 mN/m. The calculated mole ratio of protonatable guanidine groups to glyphosate was 3.3:1.

Example 6

2-dodecylguanidine (compound 15) was prepared following the procedure of Example 3. The particulars regarding the preparation are disclosed in Table 2. (Examples 1 to 15 are fully described according to the first five examples and Tables 1 and 2.)

Example 7

N-(1,1-diamino-2,5,8,11,14,17-hexaazanonadec-1-en-19-yl)heptadecanamide (compound 18) was prepared following the procedure of Example 3. The particulars regarding the preparation are disclosed in Table 2.

Example 8

Tallow$_{sat}$-guanidine (compound 17) was prepared following the procedure of Example 3. The particulars regarding the preparation are disclosed in Table 2.

Example 9

(Z)-1,1,3,3-tetramethyl-2-(octadec-9-enyl)guanidine (compound 7) was prepared following the procedure of Example 3. The particulars regarding the preparation are disclosed in Table 1.

Example 10

2-3,6,9,12,15,18-hexaazatriacontylguanidine (compound 8) was prepared following the procedure of Example 3. The particulars regarding the preparation are disclosed in Table 2.

Example 11

1,1,3,3-tetramethyl-2-3,6,9,12,15,18-hexaazatriacontylguanidine (compound 9) was prepared following the procedure of Example 3. The particulars regarding the preparation are disclosed in Table 1.

Example 12

2-hexadecylguanidine (compound 19) was prepared following the procedure of Example 3. The particulars regarding the preparation are disclosed in Table 2.

Example 13

2-hexadecyl-1,1,3,3-tetramethylguanidine (compound 10) was prepared following the procedure of Example 3. The particulars regarding the preparation are disclosed in Table 1.

Example 14

2-(2,3-diaminopropyl)tallow guanidine (compound 11) was prepared following the procedure of Example 3. The particulars regarding the preparation are disclosed in Table 2.

Example 15

2-(2,3-diaminopropyl)tallow-1,1,3,3-tetramethylguanidine (compound 12) was prepared following the procedure of Example 3. The particulars regarding the preparation are disclosed in Table 1.

TABLE 1

Examples 9-11-13-15: The guanidines (compound nos. 7, 9, 10 and 12) were prepared following the same protocol as in Example 2

| Example | 9 | 11 | 13 | 15 |
|---|---|---|---|---|
| Guanidine Name | (Z)-1,1,3,3-tetramethyl-2-(octadec-9-enyl)guanidine | 1,1,3,3-tetramethyl-2-3,6,9,12,15,18-hexaazatria-contylguanidine | 2-hexadecyl-1,1,3,3-tetramethyl-guanidine | 2-(2,3-diaminopropyl)tallow-1,1,3,3-tetramethyl-guanidine |
| Compound No. | 7 | 9 | 10 | 12 |
| Amine Name | oleylamine | 3,6,9,12,15,18-hexaazatria-contylamine | hexadecylamine | Inipol ™ DS |
| Amine weight | 100 g | 107 g | 100 g | 100 g |
| Tetramethyl-urea weight | 86.7 g | 87.2 g | 96 g | 143.2 g |
| POCl$_3$ weight | 114.4 g | 115 g | 127 g | 189 g |
| Residue weight | 101 g | 61.6 g | 110 g | 145 g |
| Yield | 74% | 43% | 78% | 90% |

TABLE 2

Examples 6-7-8-10-12-14: The guanidines (compound nos. 15, 18, 17, 8, 19 and 11) were prepared following the same protocol as in Example 3.

| Example | 6 | 7 | 8 |
|---|---|---|---|
| Guanidine Name | 2-dodecyl-guanidine | N-(1,1-diamino-2,5,8,11,14,17-hexaazanonadec-1-en-19-yl) heptadecanamide | tallow$_{sat}$-guanidine |
| Compound No. | 15 | 18 | 17 |
| Amine Name | dodecylamine | heptadecanamide | Noram ™ SH |
| Amine weight | 100 g | 100 g | 100 g |
| Cyanamide weight | 23 g | 14 g | 18.75 g |
| Residue weight | 100 g | 73 g | 70 g |
| Yield | 82% | 65% | 61% |

| Example | 10 | 12 | 14 |
|---|---|---|---|
| Guanidine Name | 2-3,6,9,12,15,18-hexa-azatriacontylguanidine | 2-hexadecyl-guanidine | 2-(2,3-diaminopropyl) tallow guanidine |
| Compound No. | 8 | 19 | 11 |
| Amine Name | 3,6,9,12,15,18-hexaazatriacontylamine | hexadecylamine | Inipol ™ DS |
| Amine weight | 119 g | 100 g | 100 g |
| Cyanamide weight | 22 g | 21.74 g | 16.2 g |
| Residue weight | 105 g | 101 g | 105 g |
| Yield | 77% | 85% | 92% |

Examples 1 to 15

| Example | 1 | 2 | 3 |
|---|---|---|---|
| Formulation Number | 1A | 2A | 3A |
| Compound Number | 5 | 16 | 6 |
| Guanidine Name | N,N,N,N-tetramethyl-(coco)guanidine | N,N,N,N-tetramethyl-(tallow$_{sat}$)guanidine | 2-cocoguanidine |
| Guanidine weight | 29.4 g | 22.9 g | 20.4 g |
| Glyphosate weight | 12.2 g | 12.2 g | 10.2 g |
| Water weight | 198.8 g | 208.3 g | 169.4 g |
| Guanidine/glyphosate mole ratio | 1.39 | 0.85 | 1.3 |
| pH at 5 g a.e./L | 4.7 | 4.6 | 4.8 |
| Diameter at 5 g a.e./L | 160 nm | nd | nd |
| Surface tension at 5 g a.e./L | 34 mN/m | nd | nd |

| Example | 4 | 5 | 6 |
|---|---|---|---|
| Formulation Number | 4A | 5A | 6A |
| Compound Number | 13 | 14 | 15 |
| Guanidine Name | PEI1800 guanidine | castor PEI1800 guanidine | 2-dodecylguanidine |
| Guanidine weight | 9 g | 15.1 g | 21 g |
| Glyphosate weight | 10.2 g | 12.2 g | 12.2 g |
| Water weight | 218.8 g | 212.7 g | 206.8 g |
| Guanidine/glyphosate mole ratio | 0.06 | 0.08 | 1.23 |
| pH at 5 g a.e./L | 4.5 | 4.7 | 4.2 |
| Diameter at 5 g a.e./L | 5/120 nm | 6 mn | 5/150 nm |
| Surface tension at 5 g a.e./L | 61.5 mN/m | 44.9 mN/m | 27.7 mN/m |

| Example | 7 | 8 | 9 |
|---|---|---|---|
| Formulation Number | 7A | 8A | 9A |

TABLE 2-continued

| Compound Number | 18 | 17 | 7 |
|---|---|---|---|
| Guanidine Name | N-(1,1-diamino-2,5,8,11,14,17-hexaazanonadec-l-en-19-yl)heptadecanamide | tallow$_{sat}$-guanidine | (Z)-1,1,3,3-tetramethyl-2-(octadec-9-enyl)guanidine |
| Guanidine weight | 61.7 g | 56.6 g | 29.3 g |
| Glyphosate weight | 10.2 g | 10.2 g | 10.2 g |
| Water weight | 128.1 g | 133.2 g | 160.5 g |
| Guanidine/glyphosate mole ratio | 2.47 | 2.96 | 1.35 |
| pH at 5 g a.e./L | 3.3 | 4.2 | 4.7 |
| Diameter at 5 g a.e./L | Nd | nd | nd |
| Surface tension at 5 g a.e./L | Nd | nd | nd |

| Example | 10 | 11 | 12 |
|---|---|---|---|
| Formulation Number | 10A | 11A | 12A |
| Compound Number | 8 | 9 | 19 |
| Guanidine Name | 2-3,6,9,12,15,18-hexaazatriacontyl-guanidine | 1,1,3,3-tetramethyl-2-3,6,9,12,15,18-hexa-azatriacontylguanidine | 2-hexadecyl-guanidine |
| Guanidine weight | 14.2 g | 30.1 g | 32.8 g |
| Glyphosate weight | 10.2 g | 10.2 g | 10.2 g |
| Water weight | 175.6 g | 159.7 g | 157 g |
| Guanidine/glyphosate mole ratio | 0.73 | 1.33 | 1.95 |
| pH at 5 g a.e./L | 4.1 | nd | nd |
| Diameter at 5 g a.e./L | nd | nd | nd |
| Surface tension at 5 g a.e./L | nd | nd | nd |

| Example | 13 | 14 | 15 |
|---|---|---|---|
| Formulation Number | 13A | 14A | 15A |
| Compound Number | 10 | 11 | 12 |
| Guanidine Name | 2-hexadecyl-1,1,3,3-tetramethyl-guanidine | 2-(2,3-diaminopropyl)tallow guanidine | 2-(2,3-diaminopropyl)tallow-1,1,3,3-tetramethylguanidine |
| Guanidine weight | 29.4 g | 19 g | 84.2 g |
| Glyphosate weight | 10.2 g | 10.2 g | 30.4 g |
| Water weight | 60.4 g | 171 g | 205.8 g |
| Guanidine/glyphosate mole ratio | 1.46 | 0.87 | 0.86 |
| pH at 5 g a.e./L | 4.5 | 4.5 | 4.8 |
| Diameter at 5 g a.e./L | nd | nd | nd |
| Surface tension at 5 g a.e./L | nd | nd | nd |

Example 16

12 formulations with different ratios of amphiphilic salt of glyphosate with guanidine and isopropyl glyphosate salt (MON0139) were prepared in 80 g water. The hydrophobic guanidines chosen are 2-(2,3-diaminopropyl)tallow guanidine and 2-(2,3-diaminopropyl)tallow-1,1,3,3-tetramethylguanidine. The mole ratios of amphiphilic glyphosate/glyphosate salt that were selected are 0/100, 5/95, 10/90, 25/75, 100/0.

| Formulation Number | Guanidine Name | Compound Number | Guanidine at 100 ga.e./kg Weight (g) | MON0139 at 100 ga.e./kg Weight (g) |
|---|---|---|---|---|
| 14B | 2-(2,3-diaminopropyl) tallow guanidine | 11 | 0 | 80 |
| 14C | 2-(2,3-diaminopropyl) tallow guanidine | 11 | 4 | 76 |
| 14D | 2-(2,3-diaminopropyl) tallow guanidine | 11 | 8 | 72 |

| Formulation Number | Guanidine Name | Compound Number | Guanidine at 100 ga.e./kg Weight (g) | MON0139 at 100 ga.e./kg Weight (g) |
|---|---|---|---|---|
| 14E | 2-(2,3-diaminopropyl) tallow guanidine | 11 | 20 | 60 |
| 14F | 2-(2,3-diaminopropyl) tallow guanidine | 11 | 40 | 40 |
| 14G | 2-(2,3-diaminopropyl) tallow guanidine | 11 | 80 | 0 |
| 15B | 2-(2,3-diaminopropyl) tallow-1,1,3,3-tetramethylguanidine | 12 | 0 | 80 |
| 15C | 2-(2,3-diaminopropyl) tallow-1,1,3,3-tetramethylguanidine | 12 | 4 | 76 |
| 15D | 2-(2,3-diaminopropyl) tallow-1,1,3,3-tetramethylguanidine | 12 | 8 | 72 |
| 15E | 2-(2,3-diaminopropyl) tallow-1,1,3,3-tetramethylguanidine | 12 | 20 | 60 |
| 15F | 2-(2,3-diaminopropyl) tallow-1,1,3,3-tetramethylguanidine | 12 | 40 | 40 |
| 15G | 2-(2,3-diaminopropyl) tallow-1,1,3,3-tetramethylguanidine | 12 | 80 | 0 |

Example 17

12 formulations with different compositions of surfactants were prepared. The hydrophobic guanidines are (Z)-1,1,3,3-tetramethyl-2-(octadec-9-enyl)guanidine and 2-hexadecyl-1,1,3,3-tetramethylguanidine. The surfactants are MON 0818, Silwet L-77®, and Triton A38. MON 0818 is an ethoxylated fatty tallow amine with an average ethylene oxide content of about 15-18 moles. Triton Ag 98 is a nonionic surfactant commercially available from Aventis. Silwet L-77® is an organosilicone surfactant commercially available from Crompton Corporation. PEG400 (polyethylene glycol with a molecular weight of 400) was also used. All of these formulations can be prepared above 200 g a.e./kg.

| Formulation Number | 9B | 9C | 9D |
|---|---|---|---|
| Guanidine Name | (Z)-1,1,3,3-tetramethyl-2-(octadec-9-enyl) guanidine | (Z)-1,1,3,3-tetramethyl-2-(octadec-9-enyl) guanidine | (Z)-1,1,3,3-tetramethyl-2-(octadec-9-enyl) guanidine |
| Compound number | 7 | 7 | 7 |
| Guanidine weight | 5.86 g | 5.86 g | 5.86 g |
| Isopropylamine weight | 2.09 g | 2.09 g | 2.09 g |
| Glyphosate weight | 8 g | 8 g | 8 g |
| MON 0818 weight | 0 g | 9.71 g | 6.48 g |
| PEG400 weight | 0 g | 0 g | 3.24 g |
| Silwet L77 weight | 0 g | 0 g | 0 g |
| A38 weight | 0 g | 0 g | 0 g |
| Water weight | 144.05 g | 134.33 g | 134.33 g |
| pH at 5 g a.e./L | 4.5 | 4.5 | 4.5 |

| Formulation Number | 9E | 9F | 9G |
|---|---|---|---|
| Guanidine Name | (Z)-1,1,3,3-tetramethyl-2-(octadec-9-enyl) guanidine | (Z)-1,1,3,3-tetramethyl-2-(octadec-9-enyl) guanidine | (Z)-1,1,3,3-tetramethyl-2-(octadec-9-enyl) guanidine |
| Compound number | 7 | 7 | 7 |
| Guanidine weight | 5.86 g | 5.86 g | 5.86 g |
| Isopropylamine weight | 2.09 g | 2.09 g | 2.09 g |
| Glyphosate weight | 8 g | 8 g | 8 g |
| MON 0818 weight | 6.48 g | 2.83 g | 3.63 g |
| PEG400 weight | 0 g | 0 g | 1.51 g |
| Silwet L77 weight | 3.24 g | 0 g | 0 g |
| A38 weight | 0 g | 2.83 g | 2.42 g |
| Water weight | 134.33 g | 138.38 g | 136.49 g |
| pH at 5 g a.e./L | 4.5 | 4.5 | 4.5 |

-continued

| Formulation Number | 13B | 13C | 13D |
|---|---|---|---|
| Guanidine Name | 2-hexadecyl-1,1,3,3-tetramethylguanidine | 2-hexadecyl-1,1,3,3-tetramethylguanidine | 2-hexadecyl-1,1,3,3-tetramethylguanidine |
| Compound number | 10 | 10 | 10 |
| Guanidine weight | 5.88 g | 5.88 g | 5.88 g |
| Isopropylamine weight | 2.09 g | 2.09 g | 2.09 g |
| Glyphosate weight | 8 g | 8 g | 8 g |
| MON 0818 weight | 0 g | 9.94 g | 6.63 g |
| PEG400 weight | 0 g | 0 g | 3.31 g |
| Silwet L77 weight | 0 g | 0 g | 0 g |
| A38 weight | 0 g | 0 g | 0 g |
| Water weight | 144.03 g | 134.09 g | 134.09 g |
| pH at 5 g a.e./L | 4.5 | 4.5 | 4.5 |

| Formulation Number | 13E | 13F | 13G |
|---|---|---|---|
| Guanidine Name | 2-hexadecyl-1,1,3,3-tetramethylguanidine | 2-hexadecyl-1,1,3,3-tetramethylguanidine | 2-hexadecyl-1,1,3,3-tetramethylguanidine |
| Compound number | 10 | 10 | 10 |
| Guanidine weight | 5.88 g | 5.88 g | 5.88 g |
| Isopropylamine weight | 2.09 g | 2.09 g | 2.09 g |
| Glyphosate weight | 8 g | 8 g | 8 g |
| MON 0818 weight | 6.63 g | 2.9 g | 3.09 g |
| PEG400 weight | 0 g | 0 g | 1.55 g |
| Silwet L77 weight | 3.31 g | 0 g | 0 g |
| A38 weight | 0 g | 2.9 g | 3.09 g |
| Water weight | 134.09 g | 138.23 g | 136.3 g |
| pH at 5 g a.e./L | 4.5 | 4.5 | 4.5 |

Example 18

The formulations 1A, 2A, 4A 5A and 6A (the formulations of examples 1, 2, 4, 5 and 6) were evaluated for herbicidal effectiveness in a greenhouse test by foliar application to a representative annual broadleaf species, velvetleaf (*Abutilon theophrasti*, ABUT) and a representative annual narrowleaf species, Japanese millet, a form of barnyardgrass (*Echinochloa crus-galli*, ECHCF). For comparative purposes, a standard commercial formulation is included in the tests as a control; it is an aqueous solution of the mono(isopropylammonium) salt of glyphosate, containing 62% by weight (680 g a.e./l) of said salt and no other formulation ingredients except water, available from Monsanto Company.

The following procedure is used for the greenhouse test.

Seeds of the plant species indicated are planted in 85 mm square pots in a soil mix which has previously been steam sterilized and prefertilized with a 14-14-14 NPK slow release fertilizer at a rate of 3.6 kg/m³. The pots are placed in a greenhouse with sub-irrigation. About one week after emergence, seedlings are thinned as needed, including removal of any unhealthy or abnormal plants, to create a uniform series of test pots.

The plants are maintained for the duration of the test in the greenhouse where they receive a minimum of 14 hours of light per day. If natural light is insufficient to achieve the daily requirement, artificial light with an intensity of approximately 475 microEinsteins is used to make up the difference. Exposure temperatures are not precisely controlled but average about 27° Celsius during the day and about 18° Celsius during the night. Plants are sub-irrigated throughout the test to ensure adequate soil moisture levels. Relative humidity is maintained at about 50% for the duration of the test. Pots are assigned to different treatments in a fully randomized experiment design with 3 replications. A set of pots is left untreated as a reference against which effects of the treatments can later be evaluated. Two sets of 3 replications are provided for treatments with control, to ensure a sound basis is available for comparison of herbicidal effectiveness of compositions of the invention.

Application of glyphosate compositions to foliage is made by spraying with a track sprayer fitted with a TeeJet 9501E nozzle calibrated to deliver a spray volume of 93 liters per hectare (l/ha) at a pressure of 166 kilopascals (kPa). Application is made when the plants are 2-3 weeks old. After treatment, pots are returned to the greenhouse until ready for evaluation.

Treatments are made using dilute aqueous compositions, prepared by dilution with water of preformulated concentrate compositions. All comparisons are made at equal glyphosate acid equivalent rates. The required degree of dilution for a glyphosate concentration composition to make a plant treatment composition is calculated from the equation $$A = RS/VC$$

where A is the volume in milliliters (ml) of the Glyphosate composition to be added to the plant treatment composition being prepared, R is the desired Glyphosate rate in terms of grams of acid equivalent per hectare (g a.e./ha, S is the total volume in milliliters (ml) of plant treatment composition being prepared, V is the application rate in liters per hectare (l/ha) of plant treatment composition, conventionally referred to as "spray volume", and C is the concentration of Glyphosate in grams of acid equivalent per liter (g a.e./l) in the Glyphosate composition.

For evaluation of herbicidal effectiveness, all plants in the test are examined by a single practiced and experienced technician, who records percent inhibition, a visual measurement of the effectiveness of each treatment by comparison with untreated plants. Inhibition of 0% indicates no effect, and inhibition of 100% indicates hat all of the plants are completely dead. Inhibition of 85% or more is in most cases considered acceptable for normal herbicidal use; however, in greenhouse tests such as the one described in the Example it is normal to apply compositions at rates which are expected to give less than 85% inhibition, as this makes it easier to discriminate among compositions having different level of effectiveness.

Results of the tests of Example 18 are given in Table 5 below.

TABLE 5

Herbicidal effectiveness data for Example 18

| Glyphosate composition | g a.e./ha | ABUTH | ECHCF |
|---|---|---|---|
| Control | 75 | 0 | 13.3 |
|  | 100 | 5 | 36.7 |
|  | 150 | 5 | 52.5 |
|  | 200 | 29.2 | 60 |
|  | 300 | 61.7 | 68.3 |
| Formulation 2A | 75 | 20.8 | 60.8 |
| (Example 2: N,N,N,N-tetramethyl- | 100 | 64.2 | 63.3 |
| (tallow$_{sat}$)guanidine) | 150 | 80.8 | 77.5 |
|  | 200 | 83.3 | 80.8 |
|  | 300 | 93 | 86.7 |
| Formulation 6A | 75 | 0 | 20 |
| (Example 6: 2-dodecylguanidine) | 100 | 0 | 55.8 |
|  | 150 | 14.2 | 71.7 |
|  | 200 | 60 | 77.5 |
|  | 300 | 75 | 85.8 |
| Formulation 1A | 75 | 3.3 | 65.8 |
| (Example 1: N,N,N,N-tetramethyl- | 100 | 51.7 | 69.2 |
| (coco)guanidine | 150 | 80.8 | 78.3 |
|  | 200 | 87.5 | 78.3 |
|  | 300 | 87.5 | 88.3 |
| Formulation 4A | 75 | 0 | 6.7 |
| (Example 4: PEI 1800-guanidine) | 100 | 0 | 9.2 |
|  | 150 | 0 | 31.7 |
|  | 200 | 0 | 37.5 |
|  | 300 | 13.3 | 50 |
| Formulation 5A | 75 | 0 | 3.3 |
| (Example 5: Castor PEI 1800-guanidine) | 100 | 0 | 13.3 |
|  | 150 | 0 | 36.7 |
|  | 200 | 0 | 45.8 |
|  | 300 | 25 | 70 |

Example 19

Substantially the same procedure as used in Example 18 is followed in a greenhouse test by foliar application to ABUTH and ECHCF. Evaluation of herbicidal effectiveness is conducted 19 DAT. The compositions included in this test are various percentages of the composition of Example 14. Results of the tests of Example 19 are given in Table 6 below.

TABLE 6

Herbicidal effectiveness data for Example 19

| Glyphosate composition | g a.e./ha | ABUTH | ECHCF |
|---|---|---|---|
| Control | 100 | 0 | 2 |
|  | 150 | 0 | 22 |
|  | 200 | 10 | 38 |
|  | 300 | 52 | 60 |
|  | 400 | 58 | 61 |
| Formulation 14B | 100 | 0 | 22 |
| (Example 14: 2-(2,3-diaminopropyl)tallow | 150 | 0 | 35 |
| guanidine at 0%) | 200 | 1 | 48 |
|  | 300 | 18 | 76 |
|  | 400 | 57 | 77 |
| Formulation 14C | 100 | 0 | 21 |
| (Example 14: 2-(2,3-diaminopropyl)tallow | 150 | 0 | 54 |
| guanidine at 5%) | 200 | 11 | 73 |
|  | 300 | 52 | 86 |
|  | 400 | 62 | 87 |
| Formulation 14D | 100 | 0 | 4 |
| (Example 14: 2-(2,3-diaminopropyl)tallow | 150 | 0 | 54 |
| guanidine at 10%) | 200 | 0 | 66 |
|  | 300 | 22 | 85 |
|  | 400 | 36 | 86.6 |
| Formulation 14E | 100 | 0 | 7 |
| (Example 14: 2-(2,3-diaminopropyl)tallow | 150 | 0 | 45 |
| guanidine at 25%) | 200 | 0 | 57 |
|  | 300 | 9 | 75 |
|  | 400 | 43 | 85 |
| Formulation 14F | 100 | 0 | 0 |
| (Example 14: 2-(2,3-diaminopropyl)tallow | 150 | 0 | 22 |
| guanidine at 50%) | 200 | 0 | 43 |
|  | 300 | 8 | 73 |
|  | 400 | 58 | 74 |
| Formulation 14G | 100 | 0 | 1 |
| (Example 14: 2-(2,3-diaminopropyl)tallow | 150 | 30 | 20 |
| guanidine at 100%) | 200 | 55 | 38 |
|  | 300 | 65 | 72 |
|  | 400 | 74 | 73 |

Example 20

Substantially the same procedure as used in Example 18 is followed in a greenhouse test by foliar application to ABUTH and ECHCF. Evaluation of herbicidal effectiveness is conducted 19 DAT. The compositions included in this test are various percentages of the composition of Example 15. Results of the tests of Example 20 are given in Table 7 below.

TABLE 7

Herbicidal effectiveness data for Example 20

| Glyphosate composition | g a.e./ha | ABUTH | ECHCF |
|---|---|---|---|
| Control | 100 | 0 | 5 |
|  | 150 | 0 | 40 |
|  | 200 | 0 | 50 |
|  | 300 | 26 | 60 |
|  | 400 | 70 | 64 |
| Formulation 15B | 100 | 0 | 11 |
| (Example 15: 2-(2,3-diaminopropyl)tallow- | 150 | 0 | 26 |
| 1,1,3,3-tetramethylguanidine at 0%) | 200 | 26 | 39 |
|  | 300 | 54 | 48 |
|  | 400 | 76 | 52 |
| Formulation 15C | 100 | 0 | 10 |
| (Example 15: 2-(2,3-diaminopropyl)tallow- | 150 | 22 | 36 |
| 1,1,3,3-tetramethylguanidine at 5%) | 200 | 26 | 70 |
|  | 300 | 64 | 72 |
|  | 400 | 77 | 79 |
| Formulation 15D | 100 | 0 | 12 |
| (Example 15: 2-(2,3-diaminopropyl)tallow- | 150 | 4 | 48 |
| 1,1,3,3-tetramethylguanidine at 10%) | 200 | 0 | 68 |
|  | 300 | 73 | 73 |
|  | 400 | 72 | 77 |

TABLE 7-continued

Herbicidal effectiveness data for Example 20

| Glyphosate composition | g a.e./ha | ABUTH | ECHCF |
|---|---|---|---|
| Formulation 15E | 100 | 0 | 34 |
| (Example 15: 2-(2,3-diaminopropyl)tallow-1,1,3,3-tetramethylguanidine at 25%) | 150 | 0 | 62 |
|  | 200 | 6 | 72 |
|  | 300 | 62 | 73 |
|  | 400 | 74 | 77 |
| Formulation 15F | 100 | 0 | 39 |
| (Example 15: 2-(2,3-diaminopropyl)tallow-1,1,3,3-tetramethylguanidine at 50%) | 150 | 0 | 50 |
|  | 200 | 51 | 72 |
|  | 300 | 64 | 79 |
|  | 400 | 82 | 77 |
| Formulation 15G | 100 | 11 | 46 |
| (Example 15: 2-(2,3-diaminopropyl)tallow-1,1,3,3-tetramethylguanidine at 100%) | 150 | 50 | 67 |
|  | 200 | 75 | 72 |
|  | 300 | 85 | 77 |
|  | 400 | 89 | 79 |

Example 21

Substantially the same procedure as used in Example 18 was followed in a greenhouse test by foliar application to ABUTH and ECHCF. Evaluation of herbicidal effectiveness was conducted 19 DAT. The compositions included in this test include those of Examples 3, 7, 8, 9, 10, 11, 13, 14, and 15. Results of the tests of Example 21 are given in Table 8 below.

TABLE 8

Herbicidal effectiveness data for Example 21

| Glyphosate composition | g a.e./ha | ABUTH | ECHCF |
|---|---|---|---|
| Control | 100 | 10 | 71.7 |
|  | 150 | 81.7 | 83.3 |
|  | 200 | 88.3 | 78.3 |
|  | 300 | 96 | 85 |
|  | 400 | 97 | 83.3 |
| Formulation 3A | 100 | 33.3 | 0 |
| (Example 3: 2-cocoguanidine) | 150 | 6.7 | 20 |
|  | 200 | 0 | 18.3 |
|  | 300 | 13.3 | 33.3 |
|  | 400 | 10 | 61.7 |
| Formulation 7A | 100 | 0 | 0 |
| (Example 7: N-(1,1-diamino-2,5,8,11,14,17-hexaazanonadec-1-en-19-yl)heptadecanamide) | 150 | 0 | 20 |
|  | 200 | 0 | 5 |
|  | 300 | 0 | 40 |
|  | 400 | 0 | 50 |
| Formulation 8A | 100 | 0 | 15 |
| (Example 8: tallow$_{sat}$-guanidine) | 150 | 0 | 3.3 |
|  | 200 | 0 | 5 |
|  | 300 | 5 | 0 |
|  | 400 | 0 | 3.3 |
| Formulation 9A | 100 | 48.3 | 58.3 |
| (Example 9: (Z)-1,1,3,3-tetramethyl-2-(octadec-9-enyl)guanidine) | 150 | 70 | 76.7 |
|  | 200 | 81.7 | 80 |
|  | 300 | 85 | 85 |
|  | 400 | 90 | 81.7 |
| Formulation 10A | 100 | 0 | 20 |
| (Example 10: 2-3,6,9,12,15,18-hexaazatriacontyl-guanidine) | 150 | 0 | 8.3 |
|  | 200 | 0 | 60 |
|  | 300 | 0 | 70 |
|  | 400 | 3.3 | 78.3 |
| Formulation 11A | 100 | 0 | 70 |
| (Example 11: 1,1,3,3-tetramethyl-2-3,6,9,12,15,18-hexaazatriacontylguanidine) | 150 | 0 | 65 |
|  | 200 | 36.7 | 71.7 |
|  | 300 | 83.3 | 81.7 |
|  | 400 | 85 | 88.3 |
| Formulation 12A | 100 | 0 | 3.3 |
| (Example 12: 2-hexadecylguanidine) | 150 | 0 | 3.3 |
|  | 200 | 0 | 20 |
|  | 300 | 0 | 6.7 |
|  | 400 | 3.3 | 13.3 |

TABLE 8-continued

Herbicidal effectiveness data for Example 21

| Glyphosate composition | g a.e./ha | ABUTH | ECHCF |
|---|---|---|---|
| Formulation 13A | 100 | 0 | 60 |
| (Example 13: 2-hexadecyl-1,1,3,3-tetramethylguanidine) | 150 | 25 | 70 |
|  | 200 | 73.3 | 73.3 |
|  | 300 | 85 | 83.3 |
|  | 400 | 97 | 80 |
| Formulation 14A | 100 | 0 | 18.3 |
| (Example 14: 2-(2,3-diaminopropyl)tallow guanidine) | 150 | 0 | 6.7 |
|  | 200 | 3.3 | 30 |
|  | 300 | 26.7 | 50 |
|  | 400 | 56.7 | 53.3 |
| Formulation 15A | 100 | 3.3 | 40 |
| (Example 15: 2-(2,3-diaminopropyl)tallow-1,1,3,3-tetramethylguanidine) | 150 | 21.7 | 43.3 |
|  | 200 | 33.3 | 55 |
|  | 300 | 73.3 | 73.3 |
|  | 400 | 85 | 73.3 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A salt of N-phosphonomethylglycine having the formula:

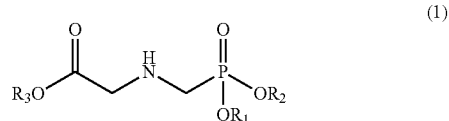

(1)

wherein $R_1$, $R_2$ and $R_3$ are independently hydrogen, sodium, potassium, ammonium, isopropylamine, n-propylamine, monoethanolamine, diethanolamine, dimethylamine, or a guanidine derivative having the formula:

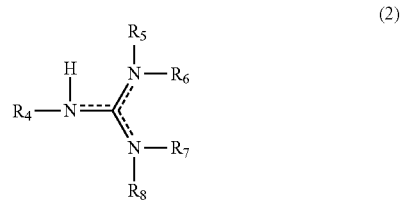

(2)

provided that at least one of $R_1$, $R_2$ and $R_3$ is the guanidine derivative;

$R_4$ is —$(CH_2)_m$—$(NR_9(CH_2)_n)_x$—$NR_{10}R_{11}$ or —$(CH_2)_m$—$CH(NH_2)CH(NH_2)R_{11}$, polyethyleneimino, $C_{12}$-$C_{18}$ alkyl, or $C_{12}$-$C_{18}$ alkenyl;

$R_5$, $R_6$, $R_7$ and $R_8$ are independently hydrogen or $C_1$-$C_5$ hydrocarbyl;

$R_9$ and $R_{10}$ are independently hydrogen or $C_1$-$C_5$ hydrocarbyl;

$R_{11}$ is $C_1$-$C_{30}$ hydrocarbyl; and m, n and x are independently an integer from 1 to 10.

2. The compound of claim 1 wherein said salt is a monobasic salt.

3. The compound of claim 1 wherein said salt is a dibasic salt.

4. The compound of claim 1 wherein said salt is a tribasic salt.

5. The compound of claim 1 wherein $R_5$, $R_6$, $R_7$ and $R_8$ are independently hydrogen or $C_1$-$C_5$ alkyl.

6. The compound of claim 1 wherein $R_4$ is 3,6,9,12,15,18-hexaazatriacontyl or tallow(2,3-diaminopropyl) and $R_5$, $R_6$, $R_7$ and $R_8$ are hydrogen.

7. The compound of claim 1 wherein $R_4$ is 3,6,9,12,15,18-hexaazatriacontyl or tallow(2,3-diaminopropyl) and $R_5$, $R_6$, $R_7$ and $R_8$ are methyl.

8. The compound of claim 1 wherein $R_4$ is polyethyleneimino and $R_5$, $R_6$, $R_7$ and $R_8$ are hydrogen.

9. The compound of claim 1 wherein $R_4$ is polyethyleneimino and $R_5$, $R_6$, $R_7$ and $R_8$ are methyl.

10. The compound of claim 1 wherein $R_4$ is dodecyl, tridecyl, tetradecyl, pentadecyl, hexadecyl, heptadecyl, octadecyl, coco, tallow, dodecenyl, tridecenyl, tetradecenyl, pentadecenyl, hexadecenyl, heptadecenyl, or octadecenyl, and $R_5$, $R_6$, $R_7$ and $R_8$ are methyl.

11. The compound of claim 1 wherein $R_4$ is dodecyl, tridecyl, tetradecyl, pentadecyl, hexadecyl, heptadecyl, octadecyl, coco, tallow, dodecenyl, tridecenyl, tetradecenyl, pentadecenyl, hexadecenyl, heptadecenyl, or octadecenyl, and $R_5$, $R_6$, $R_7$ and $R_8$ are hydrogen.

12. The compound of claim 1 wherein one of $R_1$, $R_2$ and $R_3$ is the guanidine derivative, one of $R_1$, $R_2$ and $R_3$ is sodium, potassium, ammonium, isopropylamine, n-propylamine, monoethanolamine, diethanolamine, or dimethylamine, and the other of $R_1$, $R_2$ and $R_3$ is hydrogen, sodium, potassium, ammonium, isopropylamine, n-propylamine, monoethanolamine, diethanolamine, or dimethylamine.

13. An aqueous herbicidal composition comprising the salt of N-phosphonomethylglycine of claim 1.

14. The aqueous herbicidal composition of claim 13 comprising from about 300 to about 600 grams per liter N-phosphonomethylglycine on an acid equivalent basis.

15. The aqueous herbicidal composition of claim 14 comprising from about 420 to about 600 grams per liter N-phosphonomethylglycine on an acid equivalent basis.

16. The aqueous herbicidal composition of claim 15 comprising from about 480 to about 540 grams per liter N-phosphonomethylglycine on an acid equivalent basis.

17. The aqueous herbicidal composition of claim 13 further comprising at least one surfactant.

18. The aqueous herbicidal composition of claim 13 comprising from about 1 to about 50 grams per liter N-phosphonomethylglycine on an acid equivalent basis.

19. The aqueous herbicidal composition of claim 13 comprising from about 1% to about 50% by weight of N-phosphonomethylglycine on an acid equivalent basis.

20. The aqueous herbicidal composition of claim 13 further comprising at least one co-herbicide.

21. The aqueous herbicidal composition of claim 20 wherein the co-herbicide is a water-soluble co-herbicide selected from the group consisting of acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

22. The aqueous herbicidal composition of claim 20 wherein the co-herbicide is of limited water solubility and is selected from the group consisting of acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazamox, imazosulfuron, indanofan, isoproturon, isouron, isoxaben, isoxaflutole, isoxapyrifop, lactofen, lenacil, linuron, mefenacet, mesotrione, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate.

23. A solid herbicidal composition comprising the salt of N-phosphonomethylglycine of claim 1.

24. The solid herbicidal composition of claim 23 comprising from about 10% to about 80% by weight of N-phosphonomethylglycine on an acid equivalent basis.

* * * * *